United States Patent [19]

Bianchi et al.

[11] 4,049,755

[45] Sept. 20, 1977

[54] PROCESS FOR PREPARING O,O-DIMETHYLDITHIOPHOSPHORIC ACID AND ALKALINE SALTS THEREOF

[75] Inventors: Sergio Bianchi, Bresso (Milan); Mario Bornengo, Mestre (Venezia); Alessandro Frangioni, Mogliano Veneto (Treviso), all of Italy

[73] Assignee: Montedison S.p.A., Milan, Italy

[21] Appl. No.: 539,966

[22] Filed: Jan. 10, 1975

[30] Foreign Application Priority Data

Jan. 11, 1974 Italy .................................. 19333/74

[51] Int. Cl.$^2$ ................................................ C07F 9/17
[52] U.S. Cl. ........................................ 260/987; 260/981
[58] Field of Search ............................... 260/981, 987

[56] References Cited

U.S. PATENT DOCUMENTS

| 3,070,619 | 12/1962 | Lanham | 260/981 X |
| 3,337,654 | 8/1967 | Cyba | 260/981 X |
| 3,361,668 | 1/1968 | Wiese | 260/981 X |

OTHER PUBLICATIONS

Houben–Weyl, Methoden der Organischen Chemie, 12/2/1964, pp. 684 to 688.

*Primary Examiner*—Richard L. Raymond

[57] ABSTRACT

Colorless O,O-dimethyldithiophosphoric acid is produced by reaction between a phosphorus sulfide, in particular $P_4S_7$ or $P_4S_{10}$, and methanol, at temperatures of 60 –75° C, with short reaction times, and using toluene as diluent. Colorless alkaline salts of the acid are obtained by neutralizing the toluene solution of the acid at a temperature higher than 30° C and at a pH maintained at 2 to 6.

4 Claims, No Drawings

PROCESS FOR PREPARING O,O-DIMETHYLDITHIOPHOSPHORIC ACID AND ALKALINE SALTS THEREOF

THE PRIOR ART

It is known that O,O-dimethyldithiophosphoric acid is an intermediate for the preparation of dithiophosphoric acid esters which exhibit anti-pesticide activity, such as "Malathion." It is also known alkaline salts of said acid, e.g., the Na, K and $NK_4$ salts thereof, can be used as starting materials for the preparation of various dithiophosphoric acid esters which are useful as insecticides, such as, dimethoate, phenthoate azinphos methyl and N-mercaptomethylphthalamide 5-(O,O-dimethyldithiophosphate).

As is known further, O-O-dimethyldithiophosphoric acid is also used to prepare metal salts which are widely used as additives for lubricating oils and as anti-oxidants.

Conventionally, O-O-dimethyldithiophosphoric acid has been prepared by reacting four moles of alcohol with one mole of phosphorus pentasulphide at temperatures varying from 30° to 100° C and with development of hydrogen sulphide, according to the reaction

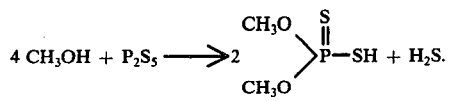 (a)

The alkaline salts of the acid have been prepared by neutralizing the acid, using an aqueous solution of hydroxides or alkaline carbonates.

In carrying out reaction (a) under the conventional conditions, and as is known, useless by-products are produced in considerable quantities. Some of the by-products are acidic, e.g., methylmercaptan and methyldithiophosphoric acid. Others, produced in even greater quantity, are neutral, e.g., the disulphide, thioanhydride and trimethyl ester of dimethyldithiophosphoric acid. Varying quantities of higher boiling substances which have not been well-identified are also produced as by-products under the conventional conditions.

The production of the by-products in substantial amounts interferes with the production of the pure acid in high yield.

As is known from the literature, the yield of useful O,O-dimethyldithiophosphoric acid obtained by the bulk reaction of phosphorus pentasulphide and methanol is only 62.8 – 64.5%. That yield can be increased to 82 – 83% of the theoretical if the oily fraction comprising the by-products is recycled, according to Italian Pat. No. 596,747 of Aug. 4, 1959.

The process requires a long reaction time (12 hours) because of the low operating temperature (20° – 30° C) and thus involves low production values.

According to another technique, described in U.S. Pat. No. 3,274,300, dialkyldithiophosphoric acid is obtained by reaction between phosphorus pentasulphide and an excess of sulphur, either as a solid solution or as a mechanical mixture. The disadvantage of that process is that at the operating temperature required dimethyldithiophosphoric acid undergoes violent decomposition and, therefore, the process is only useful for the production of dialkyldithiophosphoric acids in which the alkyl groups are higher than methyl, e.g., propyl, butyl, etc. and the reaction is between the phosphorus pentasulphide and propanol, butanol, etc.

The production of dialkyldithiophosphoric acid by the known methods requires long reaction times at relatively low temperatures, which is not only economically undesirable but often results in degradation of the product and deterioration of its quality.

According to British Patent No. 1,228,528, this drawback may be avoided, and the reaction directed to the production of the O,O-dialkyldithiophosphoric acid, by carrying out the reaction between $P_4S_{10}$ and an alcohol in the presence of a catalytic amount ($<1\%$ by weight) of $NH_3$. However, in practice, the acid obtained is strongly colored and must be purified for all uses for which a colorless product is required.

According to U.S. Pat. No. 3,573,293, dyed products are obtained by reacting phosphorus pentasulphide and alcohols or phenols in the presence of $<5\%$ of a linear or heterocyclic amine.

THE PRESENT INVENTION

One object of this invention is to provide a new process for producing, continuously or batchwise, O,O-dimethyldithiophosphoric acid, and alkaline salts thereof, which are colorless and obtained in high yield, and which process does not have the disadvantages of the known processes.

This and other objects are accomplished by the invention in accordance with which colorless O,O-dimethyldithiophosphoric acid is obtained in high yield by reacting a phosphorus sulphide, in particular $P_4S_7$ or $P_4S_{10}$, with methanol, at a temperature of 60° – 75° C, for a short reaction time (30 – 60 mins.) using toluene as the reaction diluent.

The use of toluene as diluent for the reaction is fundamental and critical inasmuch as:

1. it insures increased solubility of the phosphorus sulphide in the reacting phase (which is homogeneous) with consequent increase in the reaction rate;

2. it permits thorough stirring of the reacting mass and thus insures that the excess phosphorus sulphide required for completion of the reaction is present at all portions of the mass;

3. it prevents local overheating at the methanol/pentasulphide interface and thus permits control of the reaction and inhibits the formation of undesirable by-products and, especially, of high-boiling by-products;

4. the toluene functions as a thermal stabilizer (the methanol/toluene azeotrope boils at 85° C) and thus hinders increase in the temperature to a value at which the dimethyldithiophosphoric acid undergoes explosive decomposition; and 5. the toluene insures stability of the acid formed which, in the toluene solution, remains colorless and does not suffer degradation during storage at room temperature.

To insure the advantages mentioned, the quantity of toluene used as diluent is greater than 20% by weight of the reacting mass.

Toluene, as the reaction diluent, is particularly adapted to use with pentasulphides which react with methanol so vigorously that control of the strongly exothermic reaction is particularly critical.

In practice, the advantages of the present invention are realized by carrying out the reaction between the phosphorus pentasulphide and methanol at atmospheric pressure or at a pressure slightly higher than atmospheric, e.g.; 1 to 5 atmospheres, at a temperature of from 60° to 75° C, in an amount of toluene greater than 20% by weight of the total reacting mass ($P_4S_{10}$ + methanol + toluene), generally in an amount of 30% to 70% by weight, and in the presence of a catalytic amount of pyridine or of a pyridine base (0.01 – 0.5% by weight on the weight of the methanol).

Under said conditions, we obtain, either continuously or batchwise, a toluene solution of O,O-dimethyldithiophosphoric acid which is perfectly colorless, with a high yield of the acid (>92% based on the weight of the methanol used) and with a productivity value three times higher than can be obtained in the absence of toluene.

The toluene solutions obtained in accordance with the invention are stable in time at room temperature, also in the presence of pentasulphide.

By subsequent neutralization of the toluene solution of the acid by treatment thereof with an aqueous 10% to 30% by weight solution of an alkaline hydroxide there is obtained an aqueous solution of the alkaline-dithiophosphate of high purity, inasmuch as the neutral compounds (trimethylester, thioanhydride, disulphide) are not extracted from the alkaline solution and remain in the toluene phase which acts as purifier of the alkaline salt.

Neutralization of the toluene solution by means of a soda solution is carried out either continuously or batchwise at a temperature of from 10° to 60° C, preferably above 30° C (which is contrary to conventional practice) and at pH maintained at 2 to 6 by suitable regulation of the reactants.

The alkaline salt solution obtained is entirely colorless and stable at pH 6. No insoluble products separate from it with time and it is characterized by a low content of trimethylester (<0.1%).

The following example is given to illustrate the invention and is not intended to be limiting.

EXAMPLE 1

Into a 2 liters reactor running at operational speed, there were fed, continuously, 770 g/hr of phosphorus pentasulphide (346 moles), 435 g/hr of methanol (13.42 moles) and 652 g/hr of toluene additioned with 1 g of pyridine.

The reaction took place at atmospheric pressure, under stirring, at 70° C with an average permanence time of the reactants in the reactor of 45 minutes.

The hydrogen sulphide which developed during the reaction was removed through the reflux condenser while the reacted liquid continuously flowing out of the reactor was filtered in order to separate the entrained $P_4S_{10}$.

The toluene solution thus filtered (1725 g) appeared as a colorless liquid ($d_4^{20}$ = 1.086) stable in time, containing 58% of dimethyldithiophosphoric acid and 4 – 5% of acid and neutral reaction byproducts (disulphide thioanhydride and trimethylester of dimethyldithiophosphoric acid).

The yield in dimethyldithiophosphoric acid amounted to 91 – 93% on the methanol fed.

The toluene solution was then neutralized in a 1 lt reactor, in a continous way, into which reactor the solution was introduced under vigorous stirring together with a 20% NaOH solution (1320 g/hr).

The reaction temperature was held at 40° – 50° C (by cooling the reactor with water), while the operational pH was maintained at 5 – 6 by suitable regulation of the inflowing solutions.

The liquid flowing out of the neutralizer was rapidly mixed in an organic phase (upper phase = tolume + neutral impurities) and in an aqueous phase (lower phase = water + sodium salt of the acid).

The aqueous solution (2336 g of a 47.5 – 48% solution of sodium salt, containing 0.1 of trimethylester and 0.15% of other thiophosphorganics) appeared colorless and its pH remained unaltered between 2.5 and 6.0.

We claim:

1. Process for the continuous production of a stable alkaline solution of O,O-dimethyldithiophosphoric acid of the formula

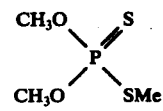

in which Me is Na, K or $NH_4$, in high yield and of a high degree of purity, and while avoiding explosions, said process consisting in reacting highly reactive phosphorus pentasulphide with methanol in an excess of 30% to 70% by weight of toluene with regard to the reacting mass, at a pressure of from 1 to 5 atm., at a temperature of from 60° to 75° C, in the presence of from about 0.01 to about 0.5% by weight, on the methanol weight, of pyridine or of a pyridine base, for an average reaction time of 30 to 60 minutes, and thereafter treating the toluene solution of O,O-dimethyldithiophosphoric acid thus obtained with an aqueous solution of an alkaline hydroxide.

2. The process according to claim 1, in which the toluene solution of O,O-dimethyldithiophosphoric acid is treated with an aqueous solution of sodium hydroxide.

3. The process according to claim 1, in which the reaction of phosphorus pentasulphide and methanol in toluene is carried out at atmospheric pressure.

4. The process according to claim 1, in which the toluene solution contains from 40% to 80% by weight of O,O-dimethyldithiophosphoric acid and is continuously treated with an aqueous solution containing from 10% to 30% by weight of an alkaline hydroxide at a temperature between 10° and 60° C and at a pH of between 2 and 6.

* * * * *